United States Patent [19]

Mueller

[11] Patent Number: 5,161,540

[45] Date of Patent: Nov. 10, 1992

[54] DEVICE FOR MONITORING A PATIENT FOR REJECTION REACTIONS OF AN IMPLANTED HEART AND METHOD OF IMPLANTING THE SAME

[75] Inventor: Johannes Mueller, Berlin, Fed. Rep. of Germany

[73] Assignee: Guido Fehling, Karlstein, Fed. Rep. of Germany

[21] Appl. No.: 705,639

[22] Filed: May 24, 1991

[30] Foreign Application Priority Data

Sep. 21, 1990 [DE] Fed. Rep. of Germany ....... 4029961

[51] Int. Cl.$^5$ ............................................. A61B 5/02
[52] U.S. Cl. ................................... 128/695; 128/630; 128/774
[58] Field of Search ............... 128/695, 774, 630, 899, 128/702-704

[56] References Cited

U.S. PATENT DOCUMENTS

| | | | |
|---|---|---|---|
| 3,639,907 | 2/1972 | Greatbatch | 340/150 |
| 3,971,363 | 7/1976 | Fletcher et al. | 128/695 |
| 4,237,900 | 12/1980 | Schulman et al. | 128/630 |
| 4,281,664 | 4/1981 | Duggan | 128/696 |
| 4,607,271 | 8/1986 | Popovic et al. | 307/309 |
| 4,813,435 | 3/1989 | Arms | 128/774 |
| 4,905,707 | 3/1990 | Davies et al. | 128/702 |

FOREIGN PATENT DOCUMENTS 2193320 2/1974 France .
2290874 11/1976 France .

OTHER PUBLICATIONS

"Myocardial Dimension Measurement System" IEEE 1979 Conference, Frontiers of Engineering in Health Care Denver, Colo., USA pp. 348-351 (18.5.1).

IEEE Transactions on Biomedical Engineering, vol. BME-33 No. 2, Feb. 1986 pp. 215-221 Design And Implementation Of An Implantable Goniometer by Troyk et al.

Primary Examiner—Lee S. Cohen
Assistant Examiner—J. Jastrzab
Attorney, Agent, or Firm—Mason, Fenwick & Lawrence

[57] ABSTRACT

To monitor a patient for rejection reactions of an implanted heart, a permanent magnet is implanted epicardially in the heart wall and a magnetically active semiconductor element, preferably a Hall generator, is implanted endocardially. Movement of the heart wall results in changes in the distance between the permanent magnet and the semiconductor element. An implantable component supplies the semiconductor element with current and measures the signal generated by the movement of the heart wall. The measured values are transmitted electromagnetically out of the body by the component and recorded extracorporeally, and stored for data transmission.

12 Claims, 1 Drawing Sheet

DEVICE FOR MONITORING A PATIENT FOR REJECTION REACTIONS OF AN IMPLANTED HEART AND METHOD OF IMPLANTING THE SAME

BACKGROUND OF THE INVENTION

The invention relates to a device for monitoring a patient for rejection reactions of an implanted heart.

Rejection of the transplanted heart poses a serious problem in heart transplants. It is therefore important to diagnose an incipient rejection reaction as soon as possible in order to be able to initiate immunosuppressive treatment in proper time. Various methods are available for monitoring the patient for incipient rejection reactions of the implanted heart.

Tissue samples are removed from the transplanted heart by endomyocardiobiopsy, and examined histologically. Invasive removal of tissue samples can only be performed in specialized hospital settings. The test cannot be repeated as often as desired, so that there is a risk of a rejection reaction beginning during the time interval between two biopsies and developing into a clinically threatening rejection crisis. Moreover, the method is only moderately representative, since only a few tissue samples can be taken each time and so will not necessarily indicate that a rejection reaction has already begun.

An electrophysiological method is also known in which the intramyocardial electrogram is measured and its changes used to diagnose the rejection reaction. Diagnosis using an intramyocardial electrogram is subject to some uncertainties since the measurement results can be influenced by other factors including fluctuations in the circadian rhythm, the stress state of the patient, and medication.

Finally, monitoring heart function using echocardiography is known. This method, which determines the movement of the heart wall using an ultrasonic echo, can likewise only be performed in specialized clinics by trained personnel. The time intervals between tests are therefore necessarily relatively long and the test is expensive. The investigative method can also be made more difficult or even rendered impossible by emphysema or adiposity of the patient, for example.

A device that can be used to monitor a patient for rejection reactions of an implanted heart is known from U.S. Pat. No. 4,237,900. It is designed to monitor the pressure in the heart.

The goal of the present invention is to provide a device which makes it possible, at reasonable cost, continuously to monitor the function of a transplanted heart, especially to detect the movements of the heart wall.

SUMMARY OF THE INVENTION

The device according to the invention makes use of the functional movement of the heart wall to diagnose incipient rejection reactions. The heart wall, especially the left ventricular heart wall, changes its thickness alternately between systole and diastole. This corresponds to a change in the distance between the endocardium and the epicardium. There is also a certain rotary motion between the endocardium and the epicardium. These movements of the heart wall are influenced by rejection reactions.

DESCRIPTION OF THE PREFERRED EMBODIMENT

Figure 1:
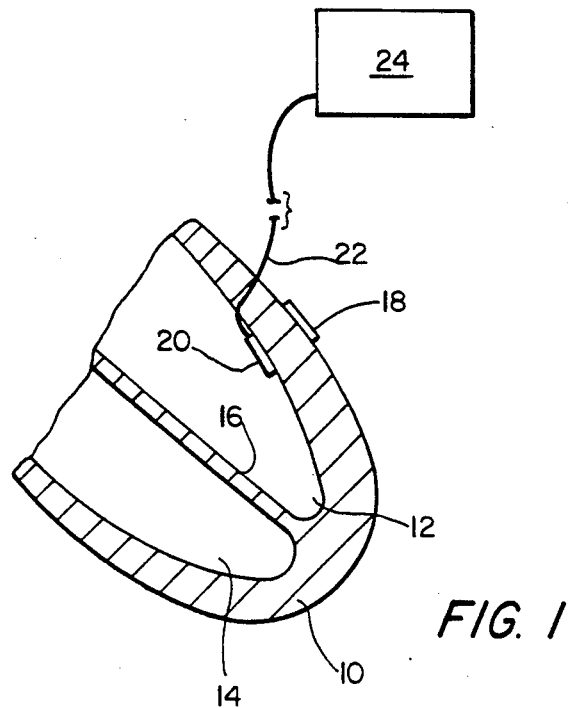
FIG. 1 is a partial cross-sectional view of a heart, with parts of the present invention applied thereto.

According to the invention, in a heart 10 having a left ventricle 12 and a right ventricle 14, and having a septum 16 between them, a sensing unit is implanted preferably in the left ventricular heart wall. The sensing unit consists of a permanent magnet 18 and a magnetically active semiconductor element 20. The permanent magnet 18 is implanted in the epicardium, while the semiconductor element 20 is implanted in the endocardium. The movement of the heart wall results in a change in the distance between the permanent magnet 18 and the magnetically active semiconductor element 20. As a result, the magnetic field strength of the permanent magnet 18 acting on the semiconductor element 10 changes, so that a signal that depends on the movement of the heart wall can be obtained from the semiconductor element. Evaluation of this signal permits diagnosis of incipient rejection reactions.

Since the movement of the heart wall is measured directly at the heart wall by the sensing unit, the measurement cannot be affected adversely by factors located outside the heart, such as emphysema or adiposity.

Figure 2:
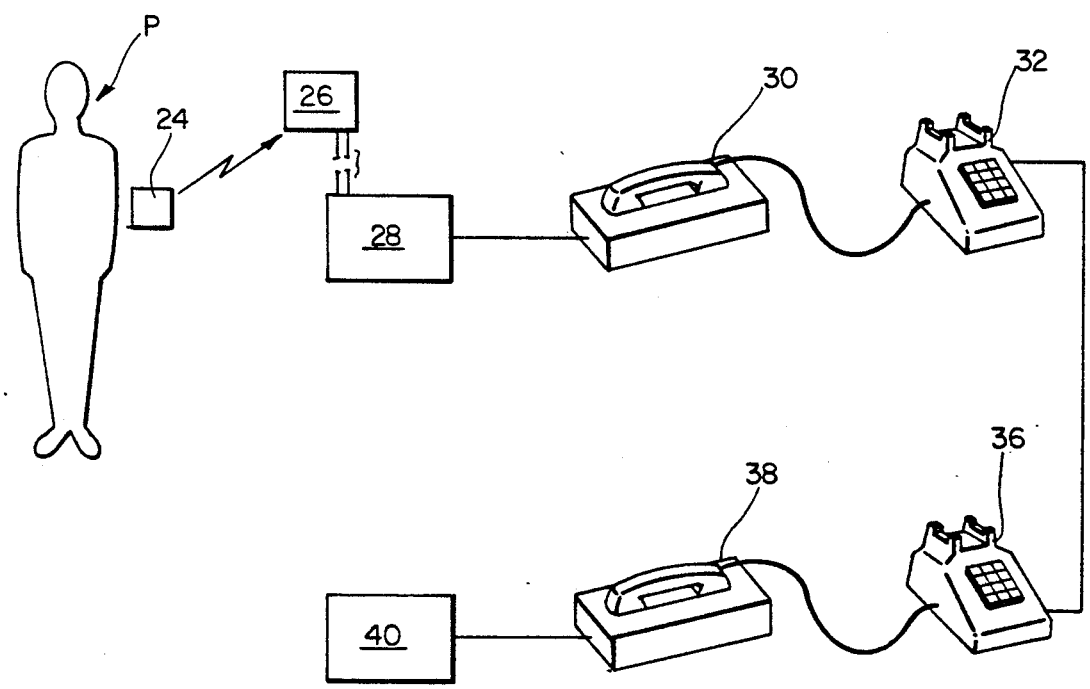
FIG. 2 is a schematic drawing of a system for monitoring a patient for rejection actions of an implanted heart in accordance with the present invention.

In addition, continuous monitoring or monitoring at short time intervals is possible when the measured values from the sensing unit are stored in an extracorporeal control and recording device 28 (see FIG. 2). The patient need not go to the clinic each time for monitoring, rather, it is merely necessary to transmit the measured values recorded at preset intervals to the clinic for evaluation. This can preferably be accomplished for example by data transmission over telephone lines.

It is especially advantageous for the sensing unit to be powered electrically by a likewise implantable component that also records the measured values and transmits them through a transmitting and receiving circuit using electromagnetic waves to the extracorporeal control and recording device. The patient can then move about practically unhampered. He need only place the antenna coil of the extracorporeal control and recording device on his body above the heart at the preset regular time intervals, for example during sleep at night. The control and recording device transmits an ON signal to the implanted component to trigger the measuring process. The measured values are transmitted from the component to the control and recording device and stored in the latter. At a later point in time, independently of the measurement, the measured values stored in the control and recording device can be transmitted to the clinic, over a data telephone line for example, and evaluated there.

Therefore, the patient need only go to the clinic when this evaluation yields results that make more detailed investigation necessary.

Since measurement of the heart wall involves relative movement between the permanent magnet and the magnetically active semiconductor element, the permanent magnet can of course be implanted in the endocardium and the semiconductor element can be implanted in the epicardium.

The magnetically active semiconductor element is preferably a Hall generator. The latter consists of a semiconductor chip which, powered by the implanted component, is traversed by a current of constant strength. The Hall voltage is tapped off at right angles to the direction of the flowing current as a measured signal.

Instead of a Hall generator, a magnetoresistor, i.e. a semiconducting resistance controlled by the magnetic field strength, can be used as a semiconductor element. Similarly, a magnetic diode can be used as a semiconductor element, changing its internal resistance as a function of the magnetic field.

In one preferred embodiment of the invention, a Hall generator is implanted endocardially in the left ventricular heart wall during the heart transplant operation, while a small permanent magnet is implanted epicardially. In addition, an electronic component 24 is implanted near the heart and connected by highly flexible connecting cables 22 with the Hall generator. The component 24 contains a battery as a power supply for the Hall generator and to supply electricity to the electronic circuits in the component. The component 24 also contains an electronic circuit for measuring the Hall voltage of the Hall generator. Finally, the component 24 contains a transmitting and receiving circuit preferably operating at a carrier frequency of 40 kHz, for example. The transmitting and receiving circuit can be induction-coupled by the electromagnetic carrier waves (see FIG. 2) with the antenna coil 26 of an extracorporeal control and recording device 28 when this antenna coil, is placed externally on the body of the patient P above the implanted heart.

To perform the monitoring process, the control and recording device 28 transmits an ON signal to the transmitting and receiving circuit to turn on the component 24. A current is then conducted by the Hall generator and the Hall voltage of the Hall generator, which changes as a function of the movement of the heart wall, is measured. The measured values are transmitted out of the patient's body by the transmitting and receiving circuit, picked up by the antenna coil 26, and stored in the control and recording device 28. After the measuring cycle programmed in the control and recording device 28 has elapsed, the component 24 is turned off again by an OFF signal transmitted by the control and recording device 28 so that the battery in the component 24 is subjected to a minimum load. The measured value stored in the control and recording device 28 can be called up by the clinic at a suitable time for evaluation, using a modem 30, telephone 32, and a telephone line 32, a telephone 36 and a modem 38 for data transmission to an evaluating apparatus 40.

I claim:

1. Apparatus for use in monitoring a patient for rejection reactions of an implanted heart comprising an electronic sensing unit implantable in the patient's body for measuring patient values and an implantable component comprising means for supplying electric energy to the sensing unit and for transmitting the values measured by the sensing unit out of the patient's body to an extracorporeal control and recording device:
   said sensing unit comprising a permanent magnet implantable in either the epicardium or the endocardium, and a semiconductor element implantable in the other of the endocardium or epicardium, and
   means for electrically connecting the semiconductor element with the component to transmit electric energy from said component to the semiconductor element and to transmit values from the semiconductor element representing variation in the thickness of the heart wall between the epicardium and the endocardium to the said component.

2. The apparatus according to claim 1, wherein said component comprises a transmitting and receiving circuit for electromagnetic waves, and extracorporeal control and recording apparatus coupled with said transmitting and receiving circuit.

3. The apparatus according to claim 2, said control and recording device comprising data transmission apparatus.

4. The apparatus according to claim 1, wherein said means for electrically connecting said semiconductor element and said component comprises flexible connecting leads.

5. The apparatus according to claim 1, said semiconductor element being a Hall generator.

6. The apparats according to claim 1, said semiconductor element being a magnetoresistor.

7. The apparatus according to claim 1, said semiconductor element being a magnetic diode.

8. The apparats according to claim 1, wherein said permanent magnet and said semiconductor element comprise means implantable on opposite portion of a heart wall for sensing change in thickness thereof without perforation of said heart wall.

9. A method of implanting an apparatus for use in monitoring a patient for rejection reactions of an implanted heart comprising:
   implanting a semiconductor in either the epicardium or the endocardium of a wall of an implanted heart,
   implanting a permanent magnet in the other of said epicardium and endocardium in operative relation with said semiconductor,
   implanting int he body of the patient a component connected by leads to said semiconductor and comprising means for supplying electric energy to said semiconductor and means for receiving and measuring variation in signal strength of said semiconductor caused by variation in the relative position of the permanent magnet and the semiconductor as caused by variation in the thickness of the heart wall of the implanted heart.

10. The method of claim 9, wherein said implanting of a component comprises implanting a component comprising a transmitting and receiving circuit for electromagnetic waves.

11. The method of claim 10, and further comprising providing extracorporeal control and recording apparats electromagnetically coupled with said transmitting and receiving circuit.

12. The method of claim 11, and further comprising providing a control and recording apparatus which comprises data transmission apparatus.

* * * * *